United States Patent
Bradley et al.

[11] Patent Number: 6,117,082
[45] Date of Patent: Sep. 12, 2000

[54] MEDICAL DIAGNOSTIC ULTRASOUND IMAGING SYSTEM AND METHOD WITH FRACTIONAL HARMONIC SEED SIGNAL

[75] Inventors: Charles E. Bradley, Burlingame; Samuel H. Maslak, Woodside; David J. Napolitano, Pleasanton, all of Calif.

[73] Assignee: Acuson Corporation, Mountain View, Calif.

[21] Appl. No.: 09/282,603

[22] Filed: Mar. 31, 1999

[51] Int. Cl.[7] .................................. A61B 8/02; A61B 8/14
[52] U.S. Cl. ............................................. 600/447; 600/458
[58] Field of Search .................................. 600/437, 442, 600/443, 447, 454, 455, 458

[56] References Cited

U.S. PATENT DOCUMENTS

| | | |
|---|---|---|
| 5,410,516 | 4/1995 | Uhlendorf et al. . |
| 5,540,090 | 7/1996 | Schutt . |
| 5,678,553 | 10/1997 | Uhlendorf et al. . |
| 5,733,527 | 3/1998 | Schutt . |
| 5,740,128 | 4/1998 | Hossack et al. . |
| 5,897,500 | 4/1999 | Zhao ........................................ 600/443 |
| 5,913,823 | 6/1999 | Hedberg et al. ....................... 600/443 |
| 6,001,063 | 12/1999 | Guracar ................................... 600/453 |
| 6,019,960 | 2/2000 | Schutt .................................... 600/453 |

*Primary Examiner*—Marvin M. Lateef
*Assistant Examiner*—Ali M. Imam
*Attorney, Agent, or Firm*—Brinks Hofer Gilson & Lione

[57] ABSTRACT

Medical diagnostic ultrasonic imaging systems and methods image at a fractional harmonic such as $f_0/2$ or $3f_0/2$, where $f_0$ is the fundamental frequency of the associated transmit beam. In order to improve fractional harmonic imaging, the transmit beam includes a fractional harmonic seed component, which may also have a center frequency of $f_0/2$ or $3f_0/2$. Multiple pulse imaging methods using transmit beams having such fractional harmonic seed components further enhance fractional harmonic imaging.

51 Claims, 8 Drawing Sheets

Fig. 10a  4.0 MHz/15% BANDWIDTH FUNDAMENTAL (—)
AND 2.0 MHz/30% BANDWIDTH SEED (--)

Fig. 10b  4.0 MHz/15% BANDWIDTH FUNDAMENTAL (—)
AND 2.0 MHz/20% BANDWIDTH SEED (--)

Fig. 10c

MEDICAL DIAGNOSTIC ULTRASOUND IMAGING SYSTEM AND METHOD WITH FRACTIONAL HARMONIC SEED SIGNAL

BACKGROUND

The following invention represents an improvement to conventional subharmonic imaging of ultrasound contrast agents. The method improves a number of characteristics including the signal-to-noise ratio, the penetration, the axial resolution, and the specificity (i.e., the sensitivity to contrast agent relative to that of tissue).

There are a number of imaging modes that have been used to image ultrasound contrast agents. Among these are the fundamental mode, the second harmonic mode, the harmonic pulse-inversion mode, the power harmonic Doppler modes, the loss-of-correlation modes, and the subharmonic mode. Each of these modes has its advantages and its disadvantages in terms of penetration, detail resolution, frame-rate, ease-of-use, and other important imaging concerns.

One of the most recent of these imaging modes, the subharmonic mode, offers potential benefit over the others in its particular combination of advantages. Most notably, subharmonic imaging has very good specificity in its sensitivity to contrast agents over its sensitivity to tissue. It is also a mode that is not dependent upon destruction of the contrast agent and is therefore a mode that can be used in continuous, as opposed to intermittent, imaging. It is also a single-pulse method and is therefore highly immune to tissue motion artifacts.

In ultrasound contrast agents, the dominant subharmonic distortion component occurs at half the frequency of the insonification (i.e., half the fundamental frequency). In a typical subharmonic imaging scenario, the system is set up to launch a pulse that occupies a frequency band centered at the fundamental frequency $f_0$, and to receive a band of frequencies centered at $f_0/2$. Echo signals at the fundamental frequency $f_0$ are rejected, typically by use of a conventional bandpass filter centered at the subharmonic frequency. Note that this imaging scenario is quite similar to second harmonic imaging, except that instead of receiving and filtering at $2*f_0$, we receive and filter at $f_0/2$.

In subharmonic imaging one of the chief concerns is that the subharmonic signal levels are, for typical B-mode imaging pulses, typically quite low. The subharmonic distortion mechanism is such that the subharmonic distortion component accumulates gradually over the duration of the pulse. If the pulse duration is short, then the subharmonic distortion will not accumulate to as large a level as would occur if the pulse duration were longer. In other words, the subharmonic response from wideband excitation is substantially less than that from narrowband excitation. In still other words, there is a tradeoff between axial resolution and signal level. For practical imaging signal levels, the pulse durations must typically be substantially (e.g., a factor of three) longer than typical B-mode pulse durations. As a consequence, the axial resolution is typically substantially worse than that of typical B-mode.

SUMMARY

In the preferred embodiments described below, the transmitted pulse is designed such that the efficiency of the contrast agent bubble in generating subharmonic distortion is improved. Simply put, these embodiments include a low level subharmonic "seed" in the transmit waveform. This seed acts to nucleate the growth of the subharmonic distortion component, which increases the efficiency of the process of subharmonic generation. This in turn provides an improvement in the subharmonic signal level or imaging bandwidth (we may trade the improved signal level off for bandwidth by using shorter duration pulses).

DETAILED DESCRIPTION OF THE PREFERRED EMBODIMENTS

General Discussion

The subharmonic distortion process differs dramatically from the usual harmonic distortion process. In order for subharmonic distortion to occur, the system must not only be nonlinear, but must be dynamically unstable as well. Unlike stable nonlinear processes, unstable nonlinear processes occur at threshold levels. Below a certain excitation level (such as incident acoustic field amplitude), there are no subharmonic distortion components generated. Harmonic distortion components, on the other hand, are present to some degree at all excitation levels (at so-called linear excitation levels they are simply present at very low levels). Subharmonic distortion components are absent until the threshold excitation level is reached. At that point the system becomes unstable with respect to the subharmonic, and the subharmonic signal appears.

The subharmonic instability (or period doubling instability) may most simply be understood in terms of sum and difference frequency interactions. For a system that is quadratically nonlinear at leading order, such as a contrast agent bubble, the nonlinear distortion process may be understood in terms of sum and difference frequency interactions. If the insonification consists of the two primary frequency components $f_1$ and $f_2$, then the bubble will respond first at those frequencies only. As the amplitudes of these primary response components grow to become large, the frequencies mix. In other words, there appear secondary response components at frequencies $f_1+f_2$ and $f_1-f_2$. These new frequency components are generated in proportion to the product of the amplitudes of the two primary frequency components. The primary signals also mix with themselves to generate response components at $2*f_1$, $2*f_2$, and DC. These new, nonlinearly generated frequency components may eventually accumulate to large enough amplitudes to mix further. The component at $f_1+f_2$, for example, may become large enough in amplitude to result in a substantial degree of interaction with the component at $2*f_2$, and generate sum and difference frequencies of $f_1+3*f_2$ and $f_2-f_1$, respectively.

If the insonification is at the single frequency $f_0$, then the self interaction leads to signals at DC and $2*f_0$. If these signals grow to sufficient levels, then an appreciable interaction between $f_0$ and $2*f_0$ occurs and yields $3*f_0$ and $f_0$. The continuation of this cascade of sum and difference frequency interactions yields the usual harmonic distortion series. This series contains the frequency components $N*f_0$, where N is a non-negative integer.

Note that the scenario outlined above with the single excitation frequency $f_0$ predicts the emergence of the harmonic distortion series $N*f_0$, but does not predict the emergence of subharmonic distortion components, which would occur at the frequencies $(N+1/2)*f_0$. That is because we have not considered the effects of dynamic instability, which is necessary for their occurrence. In order to test the stability of a solution, we consider what happens to the behavior of the system in the presence of noise. While in linear and stable nonlinear systems the presence or absence of low-level noise does not substantially change the character of the solution, if the system is an unstable nonlinear system then it can. Consider the classic problem of a particle in a potential field. The equilibrium (time-independent) solutions are given by the positions in the potential field where the field is locally flat. If there is no noise present in the analysis, then there is no distinction between stable equilibrium solutions (local minima in the potential field) and unstable ones (local maxima). If the particle is placed at one of these equilibrium solution positions, with no momentum, then the particle will remain at that position forever. If noise is added to the system, then a particle that occupies one of the unstable equilibrium points will eventually leave that position. An example of such an unstable equilibrium is a marble set atop an inverted bowl. Noise will eventually cause the initially motionless marble to move slightly off of the peak of the bowl, and to fall away from the equilibrium position. The system is destabilized and the character of the solution changes dramatically (it becomes time dependent).

Figure 1A:
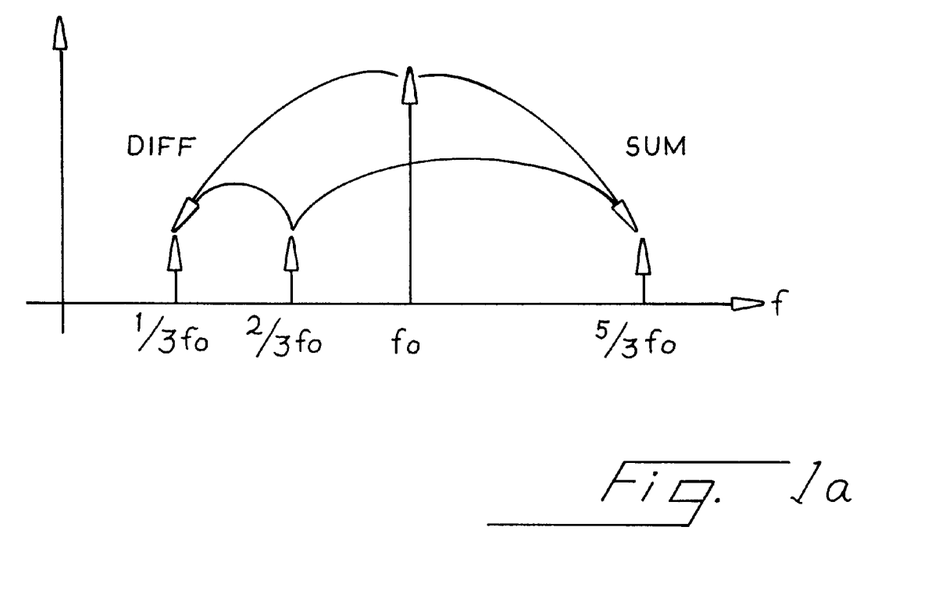
FIGS. 1A and 1B are schematic diagrams illustrating nonlinear spectral interactions.

Consider again the "frequency mixing" scenario outlined above, but now in the presence of white noise. The insonification is at $f_0$. Consider in particular the noise that occurs at $2/3*f_0$, for example. The sum and difference interactions between this component of the noise and the fundamental result in the deposition of energy at $1/3*f_0$ and $5/3*f_0$. These interactions are shown schematically in FIG. 1a. Note that the frequencies generated during this mixing process are deposited at points in the spectrum where noise already exists. In addition, the noise at these frequencies will interact with the fundamental and deposit energy elsewhere in the spectrum. In other words there is some redistribution of the noise energy, but not dramatically so.

Figure 1B:
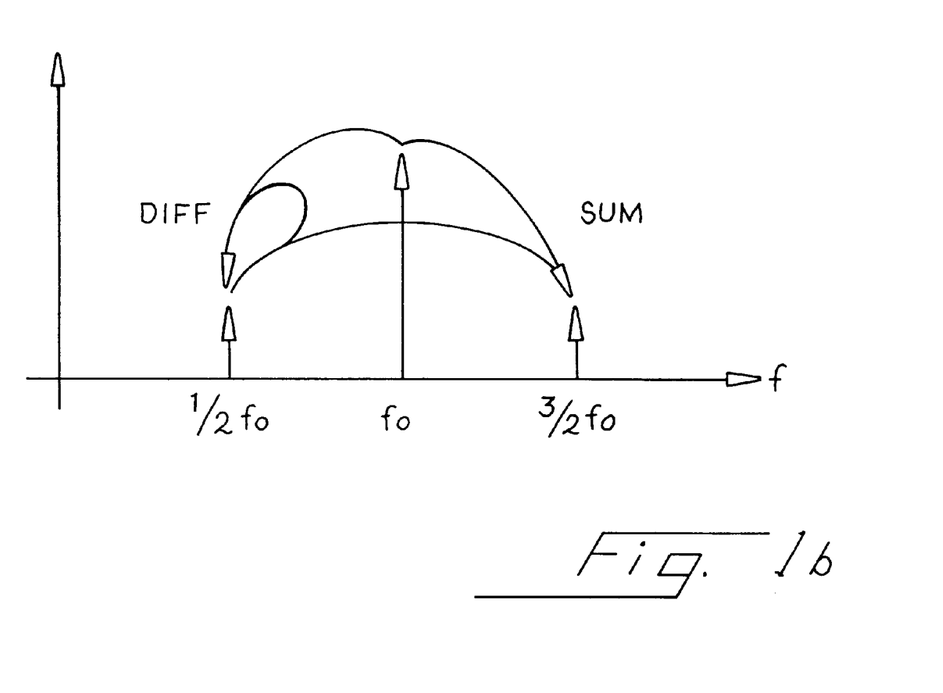

Consider next what happens to the noise at $1/2*f_0$, the subharmonic frequency. Note in particular that the difference interaction between the noise at $1/2*f_0$ and the fundamental results in the generation of a distortion component at $f_0/2$ (see FIG. 1b). This is a degenerate case in which the resultant frequency is the same as one of the two primary frequencies. The interaction causes energy to be deposited at $f_0/2$, which adds to the original noise energy at $f_0/2$ and increases its level. The interaction with the fundamental then becomes stronger (the strength of the interaction is proportional to the product of the signal amplitudes of the interacting frequencies). This strengthened interaction results in the deposition of a still greater amount of signal energy at $f_0/2$. This cascading process continues until the subharmonic level grows to such an amplitude that it saturates, or until the insonification ends. It is clear why such a process is considered unstable. If no initial energy exists at $f_0/2$, then none ever will. If, on the other hand, an arbitrarily small amount shows up, there is an energy cascade from the fundamental into the subharmonic. At the expense of the fundamental (the "pump"), the subharmonic component experiences gain.

This process is known as parametric amplification. It is associated with a threshold because below a certain fundamental signal level the interaction strength is low and therefore the rate of deposition of energy at the subharmonic frequency is low. The gain at the subharmonic depends upon how this deposition of energy compares to the loss of energy (due to nonlinear interactions, acoustic radiation, and dissipative mechanisms such as viscosity). The threshold of subharmonic instability is the drive level at which this gain becomes positive. Note the similarity to the notion of loop gain in the theory of feedback and amplifier stability.

Note that the appearance of a subharmonic spectral component comes about due only to amplification. If there were no energy at the subharmonic frequency to begin with, which is the noise-free scenario outlined above, then there would no subharmonic component ever. In other words, there needs to be some initial subharmonic energy to nucleate growth. The gain must act on a signal to result in a larger level signal. In practice, there is always some energy at the subharmonic frequency. It may be thermal noise if nothing else. In current ultrasound systems, the transmitters generate some degree of leakage signal at the subharmonic frequency which is then inadvertently launched along with the intended fundamental signal. This subharmonic transmitter leakage, though inadvertent, is then amplified parametrically to some level of subharmonic signal.

The alternative to the reliance upon noise or leakage is to include a subharmonic seed signal along with the transmitted fundamental signal. This seed signal may be adjusted in magnitude and phase (as well as other parameters such as center frequency, bandwidth, F-number, apodization, focal depth, etc.) to optimize selected parameters related to imaging. For example, the phase of the seed signal relative to that of the fundamental signal has been found to be a parameter that has two favored values (180° apart). The use of either of these favored values results in the most effective seeding in that the resultant subharmonic amplitudes are maximized for a particular seed level. The seed level may also be optimized to result in a sufficiently strong subharmonic signal that it may effectively be separated from the fundamental, but sufficiently weak that its linear backscatter from tissue doesn't result in such a substantial tissue signal that the specificity is compromised.

Figure 10A:
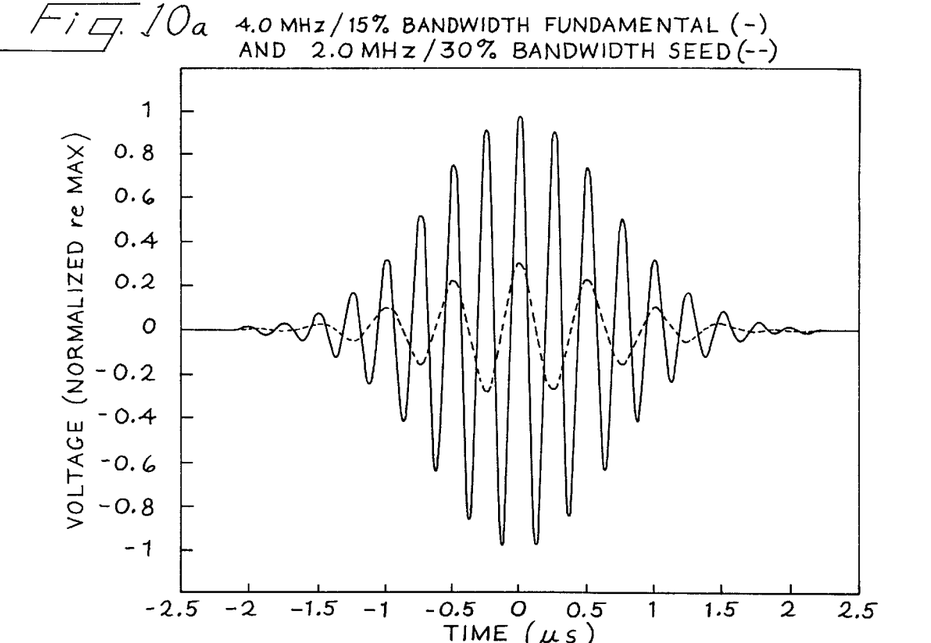
FIGS. 10a, 10b, and 10c are graphs of alternative fundamental and fractional harmonic seed components.

Examples of fundamental and seed signals are shown in FIG. 10a. The fundamental signal in this example is a 15% bandwidth Gaussian pulse of frequency 4.0 MHz, and the seed is a 2.0 MHz Gaussian pulse with the same duration (i.e., the fractional bandwidth of the seed is 30%). Note that the seed signal amplitude has been made inappropriately large for purposes of illustration (it would normally be substantially lower in amplitude). This seed signal may arise from the same transducer that transmits the fundamental signal or from a physically separate transducer.

Figure 2A:
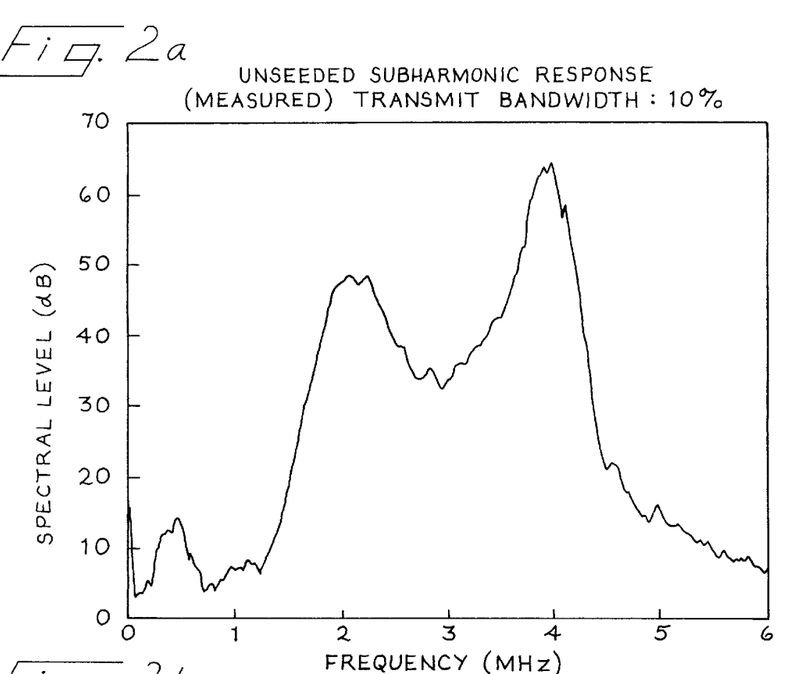
FIGS. 2A and 2B are amplitude versus frequency diagrams of subharmonic response for various transmit beams.
Figure 2B:
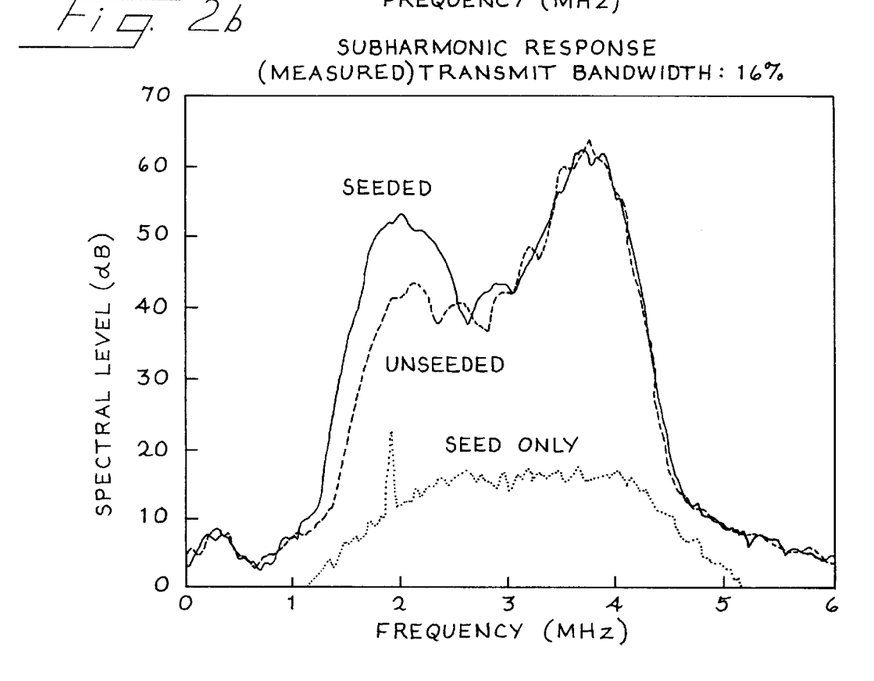

Measurements of response spectra showing the seeding effect are shown in FIGS. 2a and 2b. The transmitted pulse has a Gaussian envelope and is centered at 4.0 MHz. In the measurement shown in FIG. 2a, the fractional bandwidth of the transmitted pulse is about 10%. The response shown is the unfiltered response spectrum which clearly shows the presence of both fundamental (4.0 MHz) and subharmonic (2.0 MHz) spectral components as local maxima. The peak negative acoustic pressure is roughly 600 kPa. The resultant subharmonic spectral peak is about 15 dB below that of the fundamental. In FIG. 2b is shown the result when the transmit bandwidth is increased to about 16%. Note the drop in the subharmonic level in the absence of a seeding signal (dashed curve) due to the decreased duration of the fundamental pulse. The subharmonic does not have sufficient time to accumulate to the level of the case shown in FIG. 2a. The solid curve shows the response when a 2.0 MHz seed signal with a level about 40 dB below that of the fundamental is included in the transmitted pulse. The resultant subharmonic signal increases in level by about 10 dB. The dotted curve shows the response when the seed signal alone is transmitted. Note that the signal is so low in amplitude that it falls below the dynamic range of the receive electronics and the spectral peak is not visible above the noise floor.

There are a number of different system architectures that are capable of supporting this invention. One such architecture uses a pair of pulse generators for each transmitter channel. One is dedicated to the generation of the fundamental pulse and the other to the generation of the subharmonic seed pulse. The resultant pulses are added and sent on through the usual series of transmitter stages. As an example the Sequoia ultrasound system sold by Acuson Corporation has such an architecture. The individual waveform generators that generate the fundamental and seed signals are actually a single waveform generator that is capable of operating in a multiplexed (time interleaved) mode. With such an architecture, each channel may have the same seed level relative to the fundamental level, or they can differ. If they are the same, then the resultant transmitted beams (fundamental and seed) will have the same aperture size and apodization. If they differ, then the apodizations and/or aperture sizes can differ. Likewise, the delay profiles applied to each of these components can be identical or different, causing either the same or different focal depth (or line orientation). The line origins can differ. Element-to-element phase profiles can be the same or different. The envelope functions may be the same or may differ. The envelope functions, and therefore the pulses themselves, may be offset in time with respect to one-another or may overlap. They may have the same or differing durations. In short, with such an architecture, the fundamental and subharmonic seed may be considered to be independently transmitted beams, and any relevant beam parameters are individually adjustable.

The transmit F-numbers and apodization functions of the fundamental and seed beams may be adjusted to optimize the image uniformity with respect to depth. As subharmonic generation is a threshold phenomenon, it may be that the seed levels at the fundamental transmit focus should be less (relative to the fundamental level) than at depths removed from the transmit focus, where the fundamental level is lower and the subharmonic generation is weaker. A net offset of the delay profile associated with the seed beam with respect to that of the fundamental beam may be desirable to suppress the linearly backscattered seed signal. If the seed signal arrives at the contrast agent bubble prior to the fundamental, then the backscattered seed signal will arrive at the receive beamformer early (with respect to the fundamental). Because the beamformation process is timed based on the arrival time of the fundamental, the seed signal will be rejected to some degree. At the contrast agent bubble, however, the seed signal will endure to whatever degree the bubble resonates at that frequency. This ringing-down seed signal is still viable as a nucleation agent for the subharmonic instability.

Another architecture that supports seeding is one that generates pulses by generation of an envelope that is then modulated up to the center frequency of interest. If the architecture supports complex envelopes, then the envelope can be modified to include a complex modulation term that results in the subharmonic seed. For example, the system normally generates the real envelope function e(t) and sends this envelope to a modulation stage that multiplies this envelope by $exp(-j*w\_0*t)$, where $w\_0$ is the modulation frequency in radians per second and t is time in seconds. If the envelope is modified to be $e(t)*[1+a*exp(j*w\_0/2*t)]$, then the resultant signal after the modulation stage is $e(t)*exp(-j*w\_0*t)+a*e(t)*exp(-j*w\_0/2*t)$. Note that such a scheme can be realized in an analog system with quadrature signals that represent the real and imaginary parts of the complex signal.

Figure 10B:
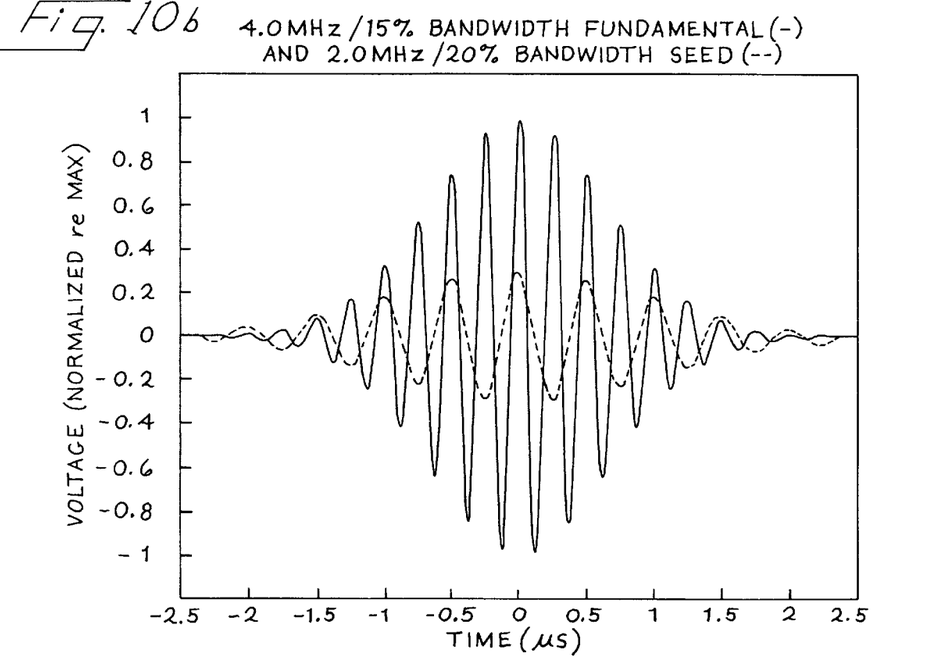
Figure 10C:
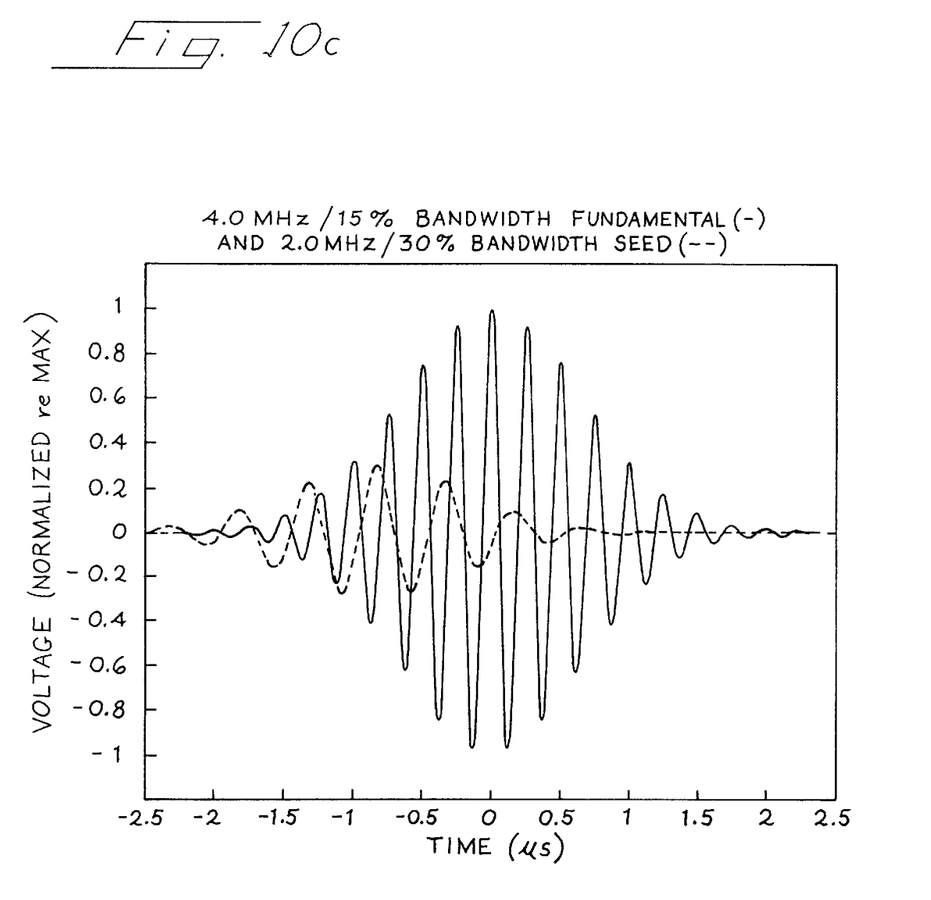

The efficiency of the seed may be improved by selecting the bandwidth of the seed such that it is smaller than that of the fundamental pulse. In this case the leading edge of the seed preceeds the leading edge of the fundamental, and seed signal is able to attain the desired amplitude by the time the fundamental reaches the threshold signal amplitude. This is effectively done with seed pulse durations that are about 50% longer than the fundamental pulse. Such a practice reduces the degree to which the seed signal continues to increase in amplitude after the subharmonic growth has been initiated. In other words, this practice allows for smaller peak seed levels, which improves the efficiency of the seed and reduces the level of the linearly backscattered seed signal (i.e., it improves specificity). An alternative approach is to initiate the generation of the seed pulse before that of the fundamental pulse, so that there is an offset in the arrival time of the two pulses; the seed preceeding the fundamental by roughly half the duration of the fundamental pulse. Such a practice similarly ensures that the seed level is nearly at its maximum value when the fundamental levels get close to the threshold value. Examples of these 'efficiency improved' seed pulses are shown in FIGS. 10b and 10c. Note again that in both of these cases, as in the case of FIG. 10a, the seed signal amplitude has been made disproportionately large for the purpose of illustration (it would normally be substantially lower in amplitude). The pulses shown in FIG. 10b are the same as those shown in FIG. 10a except that the bandwidth of the seed pulse has been reduced to 20% so that the pulse duration is 50% longer than the fundamental. In FIG. 10c the pulses are the same as those shown in FIG. 10a except that the arrival time of the seed pulse has been shifted back in time.

Note that in the 'time shifting' scenario described above, if the seed signal is shifted back in time by roughly a full pulse duration, then there is little overlap between the fundamental and the seed in the resultant transmitted signal. While not a particularly efficient seeding arrangement, it may still be effective if the Q of the bubble is large enough that the seed signal endures in the bubble oscillation until the fundamental signal acquires substantial levels. Such a transmitted waveform looks little like a superposition of fundamental seed, and more like a highly nonlinear chirp, in which the signal frequency begins at the seed frequency, endures at that frequency, and then ramps rapidly up to the fundamental frequency. Such a chirp is able to act as a combined fundamental and seed.

The seeding scenario in which the subharmonic itself is seeded has been discussed above. Alternative embodiments are to seed and image at frequencies of other components of the subharmonic series than the subharmonic. Other alternatives involve the use of seeding in a variety of two-pulse schemes. Still others address the case of seeding while using subharmonic imaging with coded transmit waveforms such as FM chirps.

One alternative to the straightforward seeding scenario outlined above is to seed at $f_0/2$, as described above, but to image using other components of the subharmonic series $(N+1/2)*f_0$, where N is a non-negative integer. Such a scenario is viable because once the subharmonic threshold is surpassed and the $f_0/2$ component of the subharmonic series shows up, all of the higher frequency components occur to some degree. An example would be to set up the system to receive, filter, and beamform based on a frequency band centered at the frequency $3*f_0/2$. The advantage of this approach is that the seed does not coincide with the imaging frequency. Any linear backscatter of the seed signal from the tissue results in a signal component at $f_0/2$ and is filtered out after reception. This improves the specificity of the imaging technique as well as the lateral resolution (due to the higher center frequency).

Another alternative is to place the seed at $(N+1/2)*f_0$ (such as $3*f_0/2$) and image at $f_0/2$. Such a seeding scenario works because the seed undergoes a difference frequency interaction with the fundamental to result in a distortion component at $f_0/2$, which in turn seeds subharmonic growth. The seed can similarly be placed at $f_0/4$. This seed will generate some response at $f_0/2$ via straightforward second harmonic distortion (the sum component of a self-interaction), which will in turn seed subharmonic growth.

In the scenarios discussed above, the system architecture was taken to be sufficiently flexible that the fundamental and seed beams may be launched from the same (or at least partially overlapping) apertures. Seeding may be enabled on a system without such flexibility if it is capable of simultaneously launching the two beams from non-overlapping apertures. These apertures may be side-by-side or may be one-inside-the-other. With either architecture the fundamental and seed beams may be launched from a probe that has separate sets of elements that specialize in the transmission and reception of fundamental and subharmonic frequency signals. These two species of elements may be interleaved along a standard array, may be placed in two side-by-side rows in elevation to form a pair of standard arrays that sit aside one another, or may be stacked one on top of the other. In the extreme, the fundamental and seed beams may be generated by completely separate probes.

Another, substantially different use of the seed is to influence the phase of the resultant subharmonic response. Such an approach can be made use of in a two-pulse scheme. Given a particular fundamental phase, there are two subharmonic phases that are preferentially excited. One of these subharmonic phases bears some generally complicated relationship to the fundamental phase. The relationship is complicated because it depends on a number of parameters, in particular the resonance frequency of the bubble and the insonification frequency and amplitude. The other subharmonic phase that can readily be excited is the opposite phase. The phase of the seed can be used to select which of these two available subharmonic phases results. Typically, for a fundamental with cosinuoidal phasing, one of the possible subharmonic responses is nearly cosinusoidal and the other is inverse cosinusoidal.

Consider a two-pulse seeding scenario in which a seeded subharmonic ultrasound line is fired twice. In the first firing, the fundamental and seed transmit pulses have some known phase relationship that results in particular phases in the fundamental and subharmonic components of the resultant ultrasound line. In the second firing, the fundamental transmit pulse is substantially the same as in the first firing, but the phase of the transmit seed pulse is inverted. In the resultant ultrasound line, the fundamental component is very similar to that from the first firing, but the subharmonic component is substantially phase inverted with respect to that from the first firing. If these two ultrasound lines are subtracted, then the fundamental components add destructively while the subharmonic components add constructively. The result is an improvement in both fundamental rejection and subharmonic signal level. Such an approach improves the rejection of the fundamental and relaxes the requirement of the filter that is otherwise used to reject the fundamental.

Figure 3A:
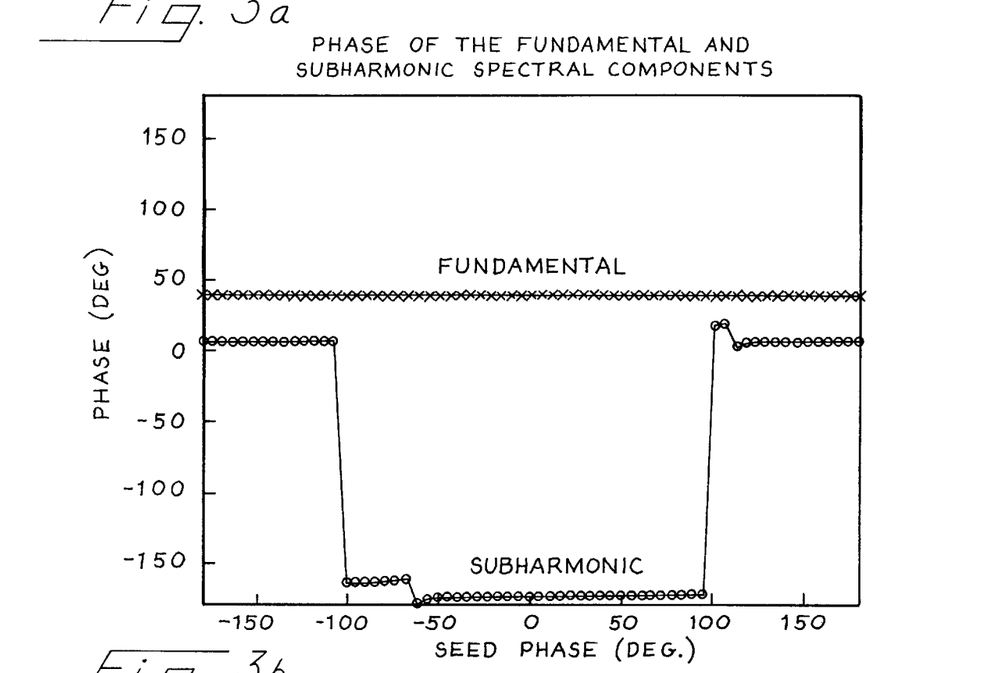
FIGS. 3A and 3B are graphs of the phase and level, respectively, of the fundamental and subharmonic spectral components as a function of seed phase.

In another version of this same two-pulse technique, the seed phases on the two firings differ by substantially less than 180°. As little as 45° is expected to work effectively. As was pointed out above, the subharmonic phase tends towards one or the other of the preferred phases. While the seed phase determines which of these two preferred phases evolves, this resultant phase is not necessarily that of the seed. The seed phase only determines which of the two preferred subharmonic phases will be selected. The results of a numerical simulation illustrate this phenomenon. FIG. 3a shows the resultant subharmonic phase when the system is excited with a cosinusoidal fundamental signal and a seed signal that differs from cosinusoidal phasing by a selected phase angle. A seed phase of 80°, for example, results in a subharmonic phase of about −180°. A seed phase of 120° results in a phase of about 0°. This characteristic, in which the subharmonic phase "snaps" to either of the two preferred phases, allows the specific phase values of the seed signals to be irrelevant for the most part. The constructive addition of the subharmonic and the destructive addition of the fundamental occur anytime the two seed phase values are chosen to straddle a phase transition point. Two such a phase transition points are seed phases of about ±100° in FIG. 3a.

Figure 3B:
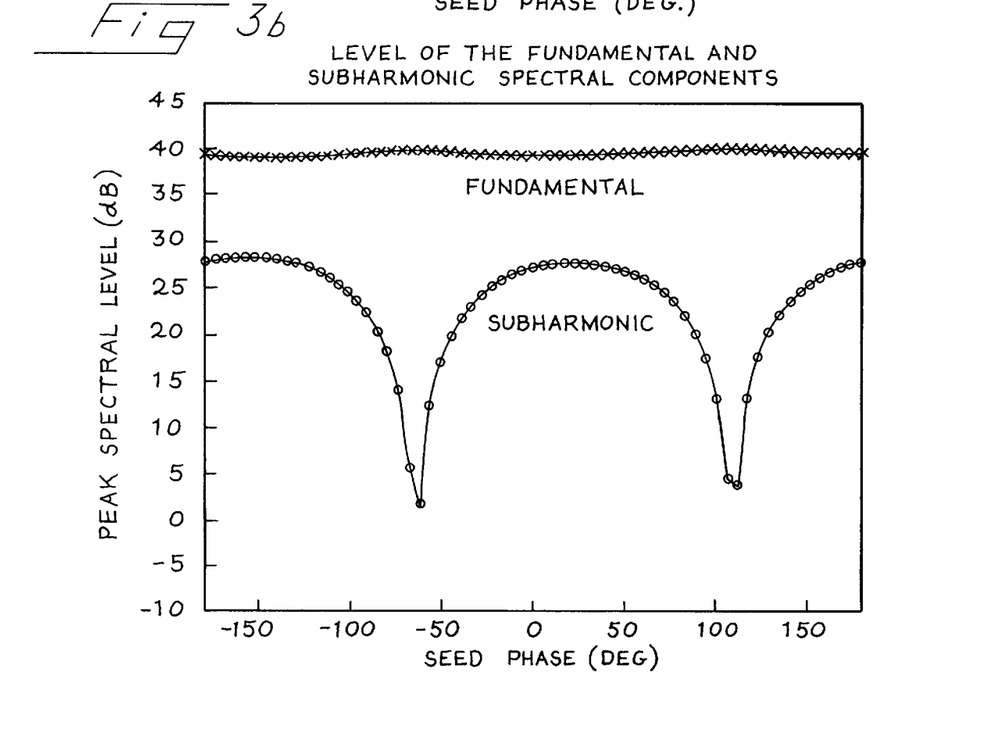

Note that the seed phase also influences the magnitude of the subharmonic response (see FIG. 3b). Seed phases of about +25 and −160° not only straddle a phase transition point and therefore result in opposite subharmonic phases, but produce the largest subharmonic response as well.

In the above two-pulse method, the objective is an improvement in both subharmonic level and fundamental rejection. Another method concerns the rejection of the linearly backscattered seed signal. In the first firing, both the fundamental and the seed beams are fired. In the resultant ultrasound line, at depths where the beam encountered contrast agent the subharmonic levels are, owing to the parametric amplification of the seed signal, quite high. At depths associated with tissue alone (no agent), the subharmonic signal is that associated with the linearly backscattered seed beam. In the second firing, we fire the seed beam alone. As the seed level is typically quite low, the signal is, at all depths, simple a linearly backscattered signal. If these two sets of line data are subtracted, the result is a measure of how much parametric gain occurred. In tissue, the signals are nearly identical, and the subtraction results in values near zero. In the contrast agent, we have a measure of the degree of gain brought about by the presence of the pump beam; i.e., the parametric gain. As the tissue image that is brought about by linear backscatter of the seed beam tends to decrease the specificity of the imaging mode, this approach is intended to reclaim some lost specificity.

Note that any of the above two-pulse schemes may be enabled using an "alternating line" mode, as described in U.S. patent application Ser. No. 09/282,396. Where in a true two-pulse mode, the two pulses are transmitted and received along the same ultrasound line, in an alternating line mode, they are fired along different (but proximate) lines. This variant leads to an increase in frame rate over the true two-pulse method, albeit with generally reduced degrees of constructive and destructive interference.

Other variants involve the use of coded excitation schemes in seeded subharmonic imaging. The transmitted fundamental and seed signals may be any of a variety of code signals other than the usual AM pulses. Examples include frequency or phase modulated pulses or sequences of such pulses. The frequency modulation may be linear (chirps) or nonlinear, monotonic or otherwise. In these cases the receive filtering is preferably configured to match the modulation of the expected return signal. This expected return signal can be calculated numerically using one of many well-known models of bubble dynamics, or may be determined empirically through experimentation.

An example of such a seeding scenario with a chirp is one in which the fundamental has a linear frequency sweep (a chirp) and the seed is a conventional pulse that is offset in time with respect to the fundamental so that the seed and fundamental overlap only at the beginning of the fundamental pulse. In this example, the fundamental begins its linear frequency sweep at frequency $f_1$ and ends it at $f_2$, and the seed is centered at $1/2*f_1$ and overlaps with the fundamental when it has a (local) frequency of $f_1$. Early in the pulse, then, we have the usual seeding circumstance and the seed nucleates the subharmonic response at $1/2*f_1$. As the fundamental sweeps upwards in frequency towards $f_2$, the fundamental begins to diverge from the previously generated subharmonic. After a time interval of dt, for example, the fundamental frequency ramps up to $f_1+df$, where df/dt is the frequency ramp rate. The subharmonic frequency that this fundamental frequency preferentially generates is $1/2*(f_1+df)$. The previously generated subharmonic had a frequency of $1/2*f_1$, but owing to its finite duration has some finite bandwidth, and includes energy at $1/2*(f_1+df)$. This energy acts as a seed that, in concert with the instantaneous fundamental frequency of $f_1+df$, will generate a subharmonic response at the frequency $1/2*(f_1+df)$. If the ramp rate df/dt is not too large, then this process will continue and the subharmonic frequency is locally moved upwards from $1/2*f_1$ to $1/2*f_2$. In this way we expect the subharmonic to ramp up in frequency at roughly half the rate of the fundamental.

This process is expected to occur for any chirps that are substantially continuous in frequency, as long as the frequency ramp rates are not too large. The maximum frequency ramp rate depends upon how rapidly the subharmonic is generated (i.e., the parametric gain), which depends upon the fundamental level and the degree of nonlinearity of the contrast agent. In other words, the maximum ramp rate is expected to depend to some degree upon the constitution of the particular contrast agent, and therefore vary from agent to agent.

In general, for a fundamental frequency modulation function f(t), the subharmonic ramp rate is expected to be roughly $1/2*f(t)$. A more exact trajectory may be calculated using one of many well-known models of bubble dynamics or may be determined empirically via measurements.

The advantage of this use of codes is the same as the advantage that such codes represent in basic fundamental mode imaging. Large duration pulses have intrinsically improved SNR, but poor axial resolution because the bandwidths are low. Coding increases the bandwidth, and therefore the axial resolution, without decreasing the duration of the pulse and therefore the SNR. This is true given that the appropriate decoding filter is used. See the co-filed U.S. patent application Ser. No. 09/282,510, the entirety of which is hereby inspected by reference, for details on the coding and decoding process. The decoding or pulse compression filter is preferably a filter that is tuned to a frequency sweep that matches the subharmonic (i.e., it is a matched filter). In the simple example above, this sweep is a linear sweep from $1/2*f_1$ to $1/2*f_2$ over the duration of the response. Such a filter causes pulse compression to a duration that corresponds to the bandwidth. The use of such codes is particularly well-suited to subharmonic imaging as the subharmonic response is, as was pointed out earlier, improved with increased pulse duration.

Note that in an alternate of the above example the seed may also be coded to match the expected subharmonic chirp. For a fundamental that has a frequency modulation given by f(t), the seed chirp is given roughly $1/2*f(t)$. Such a scheme is expected to offer little benefit over the above-described method when the ramp rates are low, because the subharmonic is then able to perform the self-seeding described above.

The benefit of the chirped seed scenario is to enable larger ramp rates.

These coded subharmonic methods may also be used with two-pulse and alternating line phase methods, as described earlier. The first ultrasound line is acquired using a transmit pulse that is composed of a coded fundamental and one of the above seeds. The second line is acquired using the same fundamental pulse but a seed with the opposite (or substantially different) phase. The two resultant ultrasound lines are subtracted to help reject the fundamental component of the signal but boost the subharmonic component. Note that the alternative seeding methods in which the higher frequency components of the subharmonic series are seeded (or used for imaging) are also viable.

Note that the specifics of any of the above methods may be optimized for performance with specific varieties of contrast agent. It may be, for example, that the seeded subharmonic response of a particular type of contrast agent is optimal at a fundamental frequency of 4.2 MHz and another works better at 3.7 MHz. Note also that some varieties of contrast agent may require a "liberation pulse" that breaks the bubble husk and releases the enclosed gas to result in a free bubble.

These methods may also be used in a triggered mode in which the trigger is supplied by the output of an electrical cardiac monitor or a delayed version of such a trigger. They may also be used in a mode that is specifically designed to detect local vascular pressure or changes in local vascular pressure.

Specific Examples

Figure 4:
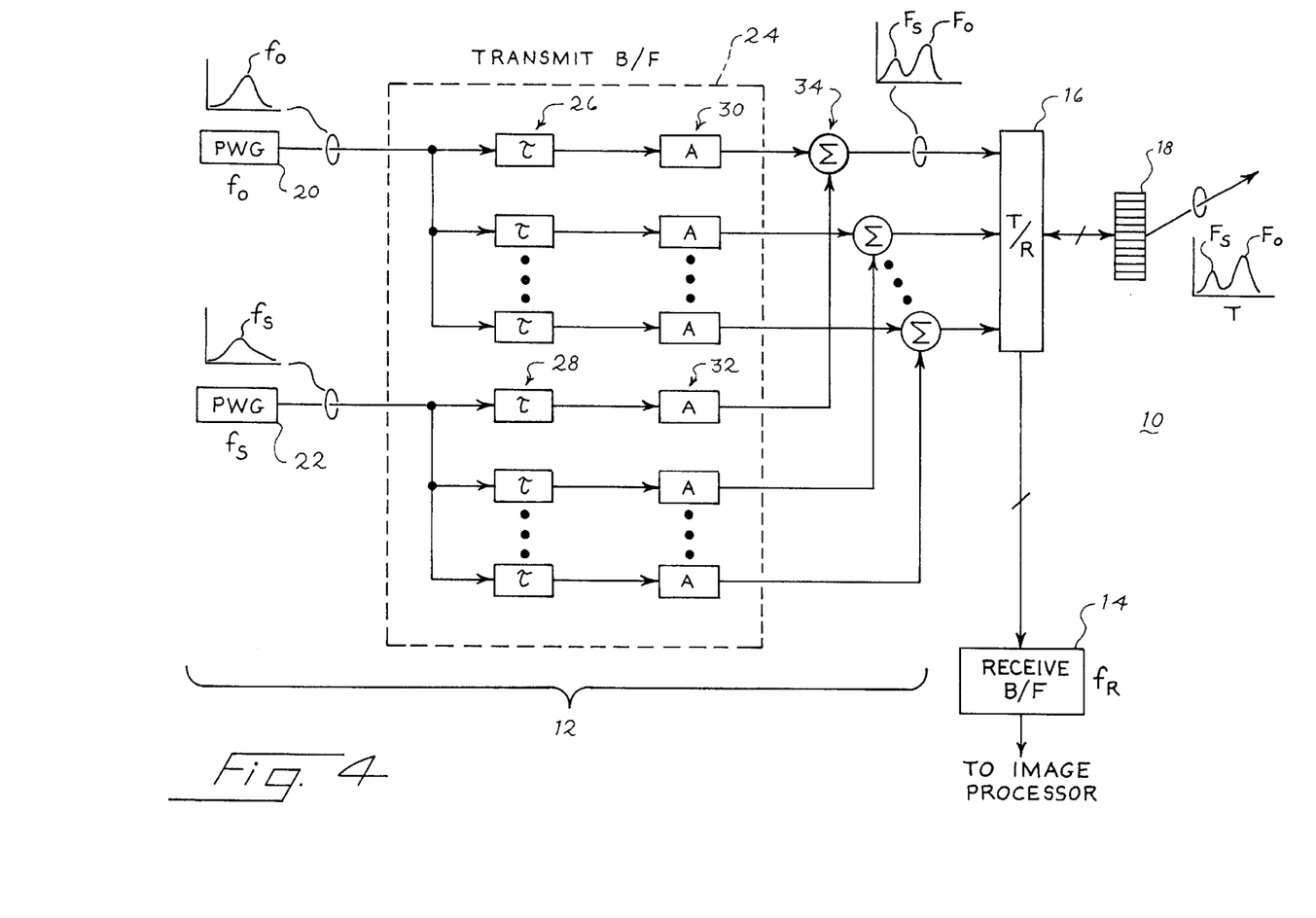
FIG. 4 is a block diagram of a medical diagnostic ultrasonic imaging system that incorporates a preferred embodiment of this invention.

FIG. 4 shows a block diagram of a medical ultrasonic diagnostic imaging system 10 that can be used to implement the present invention. The system 10 includes an ultrasonic transmitter 12 and receive beamformer 14 that are coupled via a transmit/receive switch 16 to a phased array transducer 18 such as any conventional transducer array probe for example. Any suitable transducer can be used including 1, 1.5 and 2 dimensional arrays of any desired configuration.

In the conventional manner, the transducer array 18 includes a linear array of separate transducer elements. Each element responds to a respective transmit signal supplied by the transmit/receive switch 16, and the phasings and amplitudes of these transmit signals are controlled to cause ultrasonic waves generated by the transducer elements to add coherently along a selected beam or scan line direction.

The transmitter 12 in this embodiment includes two separate programmable waveform generators 20, 22, each of which generates a respective ultrasonic pulse. These ultrasonic pulses can be considered as examples of transmit waveforms. The ultrasonic pulse generated by the programmable waveform generator 20 has a peak amplitude at a fundamental frequency $f_0$, while the ultrasonic pulse generated by the programmable waveform generator 22 has a peak amplitude at a fractional harmonic frequency $f_s$. In this embodiment, the fractional harmonic component represents an intentionally created, added or selected subharmonic seed, and the seed frequency $f_s$ takes the form $$\frac{(n+1)}{2} f_0,$$

where n is a non-negative integer. In one example, $f_s$ is equal to $f_0/2$.

The transmit waveforms generated by the programmable waveform generators 20, 22 are applied to a transmit beamformer 24. In this embodiment, the transmit beamformer 24 includes two separate sections, one for each of the transmit waveforms. The first section includes delay units 26 and amplifiers 30. The delay units 26 apply a beamformer delay profile which adjusts the timing of the first transmit waveforms on a channel-by-channel basis. In alternative embodiments, the delay units 26 can include any desired combination of time delay, phase delay and phase rotation elements. The amplifiers 30 apply a channel-by-channel apodization profile to the delayed transmit waveforms.

Similarly, the second section of the transmit beamformer 24 applies a beamformer delay profile via the delay units 28 and an apodization profile via the amplifiers 32 to the second transmit waveform generated by the programmable waveform generator 22. Since the transmit beamformer 24 includes separate sections for the two transmit waveforms, it is clear that the delay profile and/or the apodization profile applied to the first transmit waveform from the programmable waveform generator 20 can either be identical to or different from the beamformer delay profile and apodization profile applied to the second transmit waveform from the second programmable waveform generator 22.

The output signals from the transmit beamformer 24 are applied to summers 34 that sum the time-delayed, apodized, first and second transmit waveforms on a channel-by-channel basis to produce respective transmit signals. As shown in FIG. 4, each transmit signal includes a fundamental frequency component at the frequency $f_0$ of the first programmable waveform generator 20 and a fractional harmonic seed component at the frequency $f_s$ of the second programmable waveform generator 22. These transmit signals are applied to respective transducer elements of the array 18 via the transmit/receive switch 16. The transmit beam T generated by the array 18 in response to the transmit signals similarly includes a fundamental frequency component and a fractional harmonic seed component. Preferably, both the fundamental component and the seed component of the transmit beam T are apparent as local maxima in the frequency spectrum of the transmit beam T. The peak amplitude of the seed component at $f_s$ is preferably at least about −35 dB, more preferably at least about −45 dB and in some cases less than −50 dB or event −55 dB with respect to the peak amplitude of the fundamental component at $f_0$.

The system 10 of FIG. 4 provides the advantage that the fundamental component and the fractional harmonic seed component are generated substantially independently. For this reason, the fundamental and seed components of the transmit beam T can be adjusted in a flexible manner. For example, the fundamental and seed components of the transmit beam T can differ in apodization profile, peak amplitude level, aperture, focal depth, steering angle, scan line origin, pulse duration, pulse envelope, time of launch, F-number and originating transducer elements. Also, the amplitude and phase of the seed component can be selected relative to that of the fundamental component by properly programming the programmable waveform generators 20, 22. Thus, in FIG. 4 the transmit signals generated by the summers 34 include fundamental and seed components that differ in beamformer delay profile, apodization profile, aperture, and element-to-element phase profile. If desired, two or more separate programmable waveform generators may be provided for each transducer channel.

Figure 5:
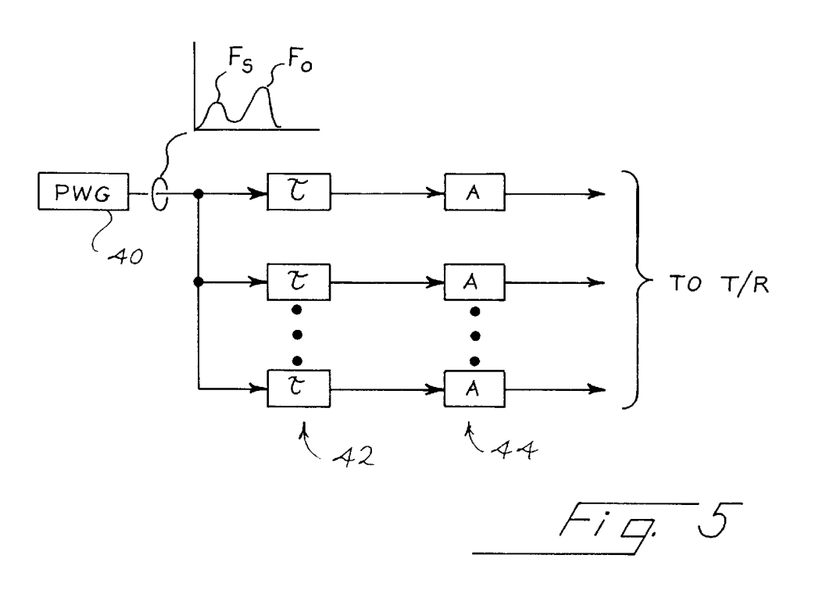
FIG. 5 is a block diagram of another ultrasonic transmitter suitable for use with this invention.

There are many alternatives to the transmitter of FIG. 4, including embodiments that are less flexible and consequently less expensive to manufacture. For example, the system of FIG. 5 uses a single programmable waveform generator 40 to form a transmit waveform that includes both the fundamental frequency component and an intentionally created or added fractional harmonic seed component. This transmit waveform is applied to delay units 42 and amplifiers 44 to generate transmit signals that are applied to the phased array via the transmit/receive switch.

Figure 6:
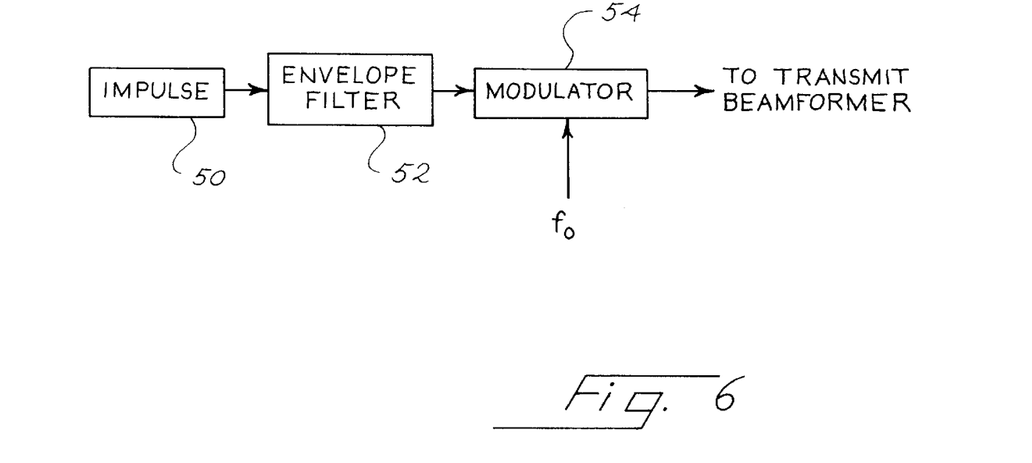
FIG. 6 is a block diagram of yet another ultrasonic transmitter suitable for use with this invention.

FIG. 6 shows another embodiment that is well-suited for analog transmitters. In the embodiment of FIG. 6, an impulse generator 50 applies an impulse to an envelope filter 52 that generates a complex envelope signal that is applied as an input to a modulator 54. The modulator 54 modulates the complex envelope signal with a fundamental frequency signal $f_0$ to generate transmit waveforms that are applied to a transmit beamformer. The complex envelope signal can be generated as described above to insure that the transmit waveforms generated by the modulator 54 include both a fundamental component and an intentionally added or created fractional harmonic seed component.

Returning to FIG. 4, the receive beamformer 14 receives echo signals from the imaged region at a receive frequency $f_r$. Typically, the receive frequency $f_r$ is set to a fractional harmonic of $f_0$. In some embodiments as described above, the receive frequency $f_r$ can be equal to the seed frequency $f_s$. For example, $f_r$ and $f_s$ can be set equal to $f_0/2$ or $3f_0/2$. In other embodiments, the receive frequency $f_r$ is set to a different frequency than the seed frequency $f_s$. For example, the seed frequency $f_s$ can be set equal to $f_0/2$ and the receive frequency $f_r$ can be set equal to $3f_0/2$, or vice versa.

Figure 7:
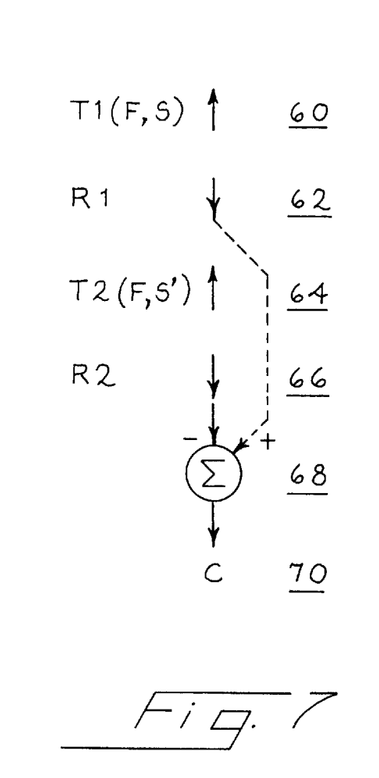
FIGS. 7, 8 and 9 are schematic diagrams of ultrasonic imaging methods that incorporate preferred embodiments of this invention.
Figure 8:
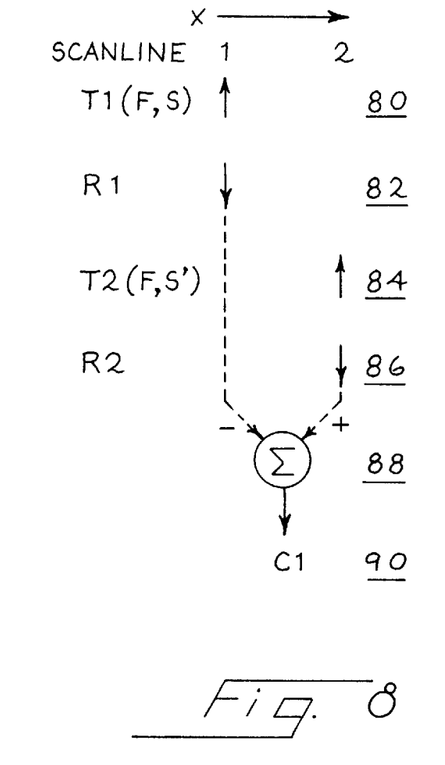
Figure 9:
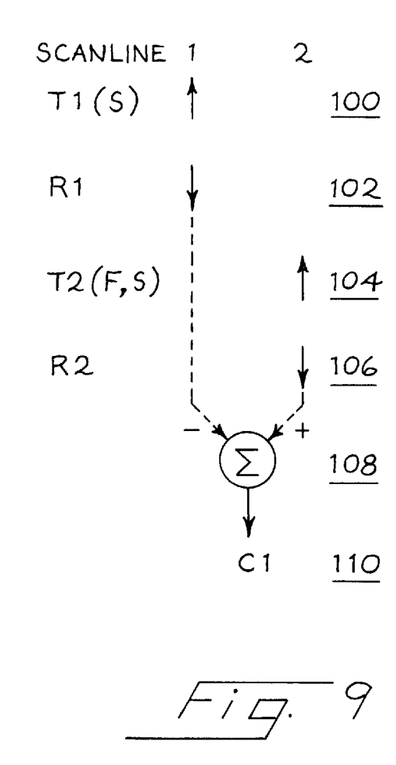

FIGS. 7–9 illustrate three multi-pulse imaging methods that can be performed with the system of FIG. 4. In the method of FIG. 7, two transmit beams are fired along the same scan line and the corresponding receive beams are combined to produce a composite signal C. The first transmit beam T1 of step 60 has a fundamental component F and a seed component S as described above. The corresponding receive signal R1 is received in step 62. The second transmit beam T2 of step 64 includes a fundamental component F identical to the fundamental component of the first transmit beam T1 and a fractional harmonic seed component S' that is identical in amplitude but different in phase from the seed component of the transmit beam T1. As explained above, the seed component S may define a first phase angle $\phi 1$ relative to the fundamental component F and the seed component S' may define a second phase angle $\phi 2$ relative to the fundamental component F. The difference $\phi 1 - \phi 2$ can be set equal to 180° or some other non-zero value as explained in detail above. The corresponding second receive beam R2 is acquired in step 66. In step 68 the first and second receive beams R1, R2 are combined with opposite polarities in a summing operation to produce the composite signal C that is applied to the image processor in step 70.

In FIG. 7 the phases of the seed components S, S' are selected such that the fractional harmonic components of the receive signals R1, R2 are approximately 180° out of phase. When the receive signals R1, R2 are combined with opposite polarity weighting factors, the fundamental components of the receive beams R1, R2 tend to cancel, while the fractional harmonic components of the receive beams R1, R2 tend to add.

FIG. 8 shows another multiple-pulse imaging method that also cancels the fundamental component F. The transmit and receive beams of steps 80–86 are identical to those of 60–66 described above, except that the first transmit beam T1 (step 80) and the first receive beam R1 (step 82) are aligned with a first scan line, while the second transmit beam T2 (step 84) and the second receive beam R2 (step 86) are aligned with a second, adjacent scan line. The combining step 88 combines the receive beams R1 and R2 and provides substantial cancellation of linear echoes of the fundamental component F to produce a combined signal C1 that is applied in step 90 to an image processor. In practice, the method of FIG. 8 would be repeated across a larger portion of a frame, with transmit beams similar to the transmit beams T1 being used for odd-numbered scan lines and transmit beams similar to the transmit beam T2 used for even-numbered scan lines. Each adjacent pair of scan lines would be combined in a summing operation to produce a related combined signal. In this way, the advantage of this multiple-pulse imaging method is obtained without any substantial decrease in frame rate. FIG. 8 represents an example of an alternative line imaging mode. Such imaging modes are described in greater detail in co-pending U.S. patent application Ser. No. 09/282,396, the entirety of which is hereby incorporated by reference.

FIG. 9 shows another multiple-pulse imaging method. In step 100 transmit beam T1 is fired along scan line 1. In this embodiment, transmit beam T1 includes a seed component S but no accompanying fundamental component F. The associated receive beam R1 is acquired on scan line 1 in step 102 and stored. In step 104 a second transmit beam T2 is fired along scan line 2. The second transmit beam T2 includes both a fractional harmonic seed component S, identical to the seed component of the transmit beam T1, in combination with a fundamental component F. The associated receive beam R2 is acquired in step 106 along scan line 2, and then in step 108 the receive beam 2 is combined with the receive beam 1 in a summing operation. Note that opposite polarity summing weights are used such that linear echoes of the seed components are cancelled from the combined signal C1 that is applied in step 110 to an image processor. The method of FIG. 9 can readily be modified to place the transmit beams T1, T2 and the receive beams R1, R2 on the same scan line.

Though the multiple-pulse imaging methods described above have combined only two receive beams, in alternative embodiments three or more receive beams may be combined to produce a composite signal, and multiple simultaneous receive beams may be acquired from a single transmit beam.

CONCLUSION

From the foregoing, it should be apparent that improved ultrasonic imaging methods and systems have been described that provide enhanced fractional harmonic imaging.

The foregoing detailed description has illustrated only a few of the many forms that this invention can take. For this reason, this detailed description is intended only by way of example. It is only the following claims, including all equivalents, that are intended to define the scope of this invention.

What is claimed is:

1. An ultrasonic transmitting method for a medical diagnostic ultrasound imaging system, said method comprising the following steps:
   (a) generating a set of beamformed ultrasonic transmit signals characterized by a fundamental frequency component;
   (b) including in step (a) the step of adding a fractional harmonic seed component to the transmit signals; and
   (c) applying the transmit signals to a medical diagnostic ultrasound transducer probe.

2. The method of claim 1 wherein step (b) comprises the step of:
   (b1) selecting amplitude of the fractional harmonic seed component relative to amplitude of the fundamental frequency component.

3. The method of claim 1 or 2 wherein step (b) comprises the step of:
   (b2) selecting phase of the fractional harmonic seed component relative to phase of the fundamental frequency component.

4. The method of claim 1 wherein steps (a) and (b) comprise the step of:
   programming a programmable waveform generator with a programmed waveform that contributes to both the fundamental frequency component and the fractional harmonic seed component.

5. The method of claim 1 wherein steps (a) and (b) comprise the steps of:
   generating a first waveform that selectively contributes to the fundamental frequency component;
   generating a second waveform that selectively contributes to the fractional harmonic seed component; and
   combining the first and second waveforms.

6. The method of claim 5 wherein the first and second waveforms are beamformed waveforms.

7. The method of claim 5 further comprising the step of:
   beamforming the combined first and second waveforms.

8. The method of claim 1 wherein step (b) comprises the steps of:
   providing a complex envelope signal that is modulated at a fractional harmonic frequency; and
   modulating the complex envelope signal at a fundamental frequency.

9. The method of claim 1 further comprising the step of:
   receiving echo signals generated in response to the transmit signals at a fractional harmonic frequency different from that of the seed component.

10. The method of claim 1 further comprising the step of:
    receiving echo signals generated in response to the transmit signals at a fractional harmonic frequency corresponding to that of the seed component.

11. The method of claim 1 wherein the fundamental frequency component and the fractional harmonic seed component form respective local maxima in a frequency spectrum of the transmit signals.

12. The method of claim 1 wherein steps (a) and (b) comprise the step of generating the transmit signals as frequency modulated pulses.

13. The method of claim 1 wherein steps (a) and (b) comprise the step of generating the fundamental frequency component and the fractional harmonic seed component as respective frequency coded transmit pulses.

14. An ultrasonic transmitter for a medical diagnostic imaging system, said transmitter comprising:
- a plurality of transmit waveform generators;
- a transmit beamformer responsive to the transmit waveform generators to generate a plurality of ultrasonic transmit signals; and
- a medical diagnostic ultrasound transducer array comprising a plurality of transducer elements responsive to the transmit signals to generate at least one transmit beam, said transmit beam comprising both a fundamental frequency component and fractional harmonic seed component.

15. The invention of claim 14 wherein the fundamental frequency component and the fractional harmonic seed component differ in apodization.

16. The invention of claim 14 wherein the fundamental frequency component and the fractional harmonic seed component differ in aperture.

17. The invention of claim 14 wherein the fundamental frequency component and the fractional harmonic seed component differ in focal depth.

18. The invention of claim 14 wherein the fundamental frequency component and the fractional harmonic seed component differ in steering angle.

19. The invention of claim 14 wherein the fundamental frequency component and the fractional harmonic seed component differ in scan line origin.

20. The invention of claim 14 wherein the fundamental frequency component and the fractional harmonic seed component differ in duration.

21. The invention of claim 14 wherein the fundamental frequency component and the fractional harmonic seed component differ in envelope function.

22. The invention of claim 14 wherein the fundamental frequency component and the fractional harmonic seed component differ in time of launch.

23. The invention of claim 14 wherein the fundamental frequency component and the fractional harmonic seed component differ in originating transducer elements.

24. The invention of claim 14 wherein the fundamental frequency component and the fractional harmonic seed component differ in F-number.

25. The invention of claim 14 wherein the fundamental frequency component and the fractional harmonic seed component differ in bandwidth.

26. The invention of claim 14 wherein the fundamental frequency component and the fractional harmonic seed component form respective local maxima in a frequency spectrum of the transmit beam.

27. The invention of claim 26 wherein the fundamental frequency components are greater in peak amplitude than the fractional harmonic seed components by no less than about 35 dB.

28. The invention of claim 26 wherein the fundamental frequency components are greater in peak amplitude than the fractional harmonic seed components by no less than about 45 dB.

29. The invention of claim 26 wherein the fundamental frequency components are greater in peak amplitude than the fractional harmonic seed components by no less than about 50 dB.

30. The invention of claim 14 wherein the transmit signals comprise frequency modulated pulses.

31. The invention of claim 14 wherein the fundamental frequency component and the fractional harmonic seed component comprise respective frequency modulated pulses.

32. An ultrasonic transmitter for a medical diagnostic imaging system, said transmitter comprising:
- a plurality of transmit waveform generators; and
- a transmit beamformer responsive to the transmit waveform generators to generate a plurality of ultrasonic transmit signals;
- said transmit signals comprising both a fundamental frequency component and a fractional harmonic seed component.

33. The invention of claim 32 wherein the fundamental frequency components and the fractional harmonic seed components differ in beamformer delay profile.

34. The invention of claim 32 wherein the fundamental frequency components and the fractional harmonic seed components differ in apodization profile.

35. The invention of claim 32 wherein the fundamental frequency components and the fractional harmonic seed components differ in aperture.

36. The invention of claim 32 wherein the fundamental frequency components and the fractional harmonic seed components differ in element-to-element phase profile.

37. The invention of claim 32 wherein the fundamental frequency component and the fractional harmonic seed component form respective local maxima in a frequency spectrum of the transmit signals.

38. The invention of claim 37 wherein the fundamental frequency components are greater in peak amplitude than the fractional harmonic seed components by no less than about 35 dB.

39. The invention of claim 37 wherein the fundamental frequency components are greater in peak amplitude than the fractional harmonic seed components by no less than about 45 dB.

40. The invention of claim 37 wherein the fundamental frequency components are greater in peak amplitude than the fractional harmonic seed components by no less than about 50 dB.

41. The invention of claim 32 wherein the transmit signals comprise frequency modulated pulses.

42. The invention of claim 32 wherein the fundamental frequency component and the fractional harmonic seed component comprise respective frequency modulated pulses.

43. An ultrasonic transmitting method for a medical diagnostic ultrasound imaging system, said method comprising the following steps:
- (a) directing a first ultrasonic transmit beam into a first region of a body, said first beam comprising a first fundamental frequency component and a first fractional harmonic seed component; and
- (b) directing a second ultrasonic transmit beam into the first region of the body, said second beam comprising a second fundamental frequency component and a second fractional harmonic seed component;
- wherein the first fractional harmonic seed component is phased relative to the first fundamental frequency component differently than the second fractional harmonic seed component is phased relative to the second fundamental frequency component.

44. An ultrasonic transmitting method for a medical diagnostic ultrasound imaging system, said method comprising the following steps:

(a) directing a first ultrasonic transmit beam into a first region of a body, said first beam comprising a first fundamental frequency component and a first fractional harmonic seed component; and (b) directing a second ultrasonic transmit beam into the first region of the body, said second beam comprising a second fractional harmonic seed component and a second fundamental frequency component that is substantially reduced in amplitude as compared with the first fundamental frequency component.

45. The method of claim 43 or 44 wherein steps (a) and (b) direct the first and second transmit beams along a single scan line.

46. The method of claim 43 or 44 wherein steps (a) and (b) direct the first and second transmit beams along respective spatially distinct scan lines.

47. The method of claim 43 wherein the first fractional harmonic seed component and the first fundamental frequency component define a phase angle $\phi 1$, wherein the second fractional harmonic seed component and the second fundamental frequency component define a phase angle $\phi 2$, and wherein $\phi 1$ and $\phi 2$ differ by about 180°.

48. The method of claim 44 wherein the second fundamental frequency component is substantially absent from the second ultrasonic transmit beam.

49. The method of claim 43 or 44 further comprising the step of:

acquiring echo signals generated in response to the transmit beams at a fractional harmonic frequency different from that of the fractional harmonic seed components.

50. The method of claim 43 or 44 further comprising the step of:

acquiring echo signals generated in response to the transmit beams at a fractional harmonic frequency corresponding to that of the fractional harmonic seed components.

51. The method of claim 43 or 44 further comprising the steps of:

acquiring at least first and second receive beams in response to the first and second transmit beams; and combining the first and second receive beams.

* * * * *